US00PP17468P2

(12) United States Plant Patent
Oudshoorn

(10) Patent No.: US PP17,468 P2
(45) Date of Patent: Mar. 6, 2007

(54) ***PHLOX* PLANT NAMED 'DELILAH'**

(50) Latin Name: *Phlox paniculata*
Varietal Denomination: Delilah

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 35 days.

(21) Appl. No.: 11/151,833

(22) Filed: Jun. 14, 2005

(51) Int. Cl.
*A01H 5/00* (2006.01)

(52) U.S. Cl. ..... Plt./320
(58) Field of Classification Search ..... Plt./320
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Phlox* plant named 'Delilah', characterized by its upright and strong plant habit; strong foliage; red purple-colored flowers; freely and continuous flowering habit; and good garden performance.

2 Drawing Sheets

Botanical designation: *Phlox paniculata.*
Cultivar denomination: 'Delilah'.

BACKGROUND OF THE INVENTION

The present Invention relates to a new and distinct cultivar of *Phlox* plant, botanically known as *Phlox paniculata,* and hereinafter referred to by the cultivar name Delilah.

The new *Phlox* is a product of a planned breeding program conducted by the Inventor in Rijpwetering, The Netherlands. The objective of the breeding program was to create new *Phlox* cultivars with attractive flower coloration.

The new *Phlox* originated from a cross-pollination made by the Inventor in 1998 in Rijpwetering, The Netherlands of the *Phlox paniculata* cultivar Lizzy, disclosed in U.S. Plant Pat. No. 11,574, as the female, or seed, parent with the *Phlox paniculata* cultivar Rowie, not patented, as the male, or pollen, parent. The new *Phlox* was discovered and selected by the Inventor as a flowering plant within the progeny of the stated cross-pollination in a controlled environment in Rijpwetering, The Netherlands in 1999.

Asexual reproduction of the new cultivar by terminal cuttings at Rijpwetering, The Netherlands since 2000, has shown that the unique features of this new *Phlox* are stable and reproduced true to type in successive generations.

SUMMARY OF THE INVENTION

Plants of the cultivar Delilah have not been observed under all possible environmental conditions. The phenotype may vary somewhat with variations in environment such as temperature and light level without, however, any variance in genotype.

The following traits have been repeatedly observed and are determined to be the unique characteristics of 'Delilah'. These characteristics in combination distinguish 'Delilah' as a new and distinct cultivar of *Phlox:*

1. Upright and strong plant habit.
2. Strong foliage.
3. Red purple-colored flowers.
4. Freely and continuous flowering habit.
5. Good garden performance.

Plants of the new *Phlox* differ primarily from plants of the parent cultivars primarily in flower color as plants of the cultivar Lizzy have lighter red purple-colored flowers and plants of the cultivar Rowie have pink-colored flowers.

Plants of the new *Phlox* can be compared to the *Phlox paniculata* cultivar Van Gogh, not patented. In side-by-side comparisons conducted in Rijpwetering, The Netherlands, plants of the new *Phlox* differed from plants of the cultivar Van Gogh primarily in plant height as plants of the new *Phlox* were much shorter than plants of the cultivar Van Gogh.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Phlox.*

The photograph on the first sheet comprises a side perspective view of a typical flowering plant of 'Delilah'.

The photograph at the top of the second sheet is a close-up view of typical flowers of 'Delilah'. The photograph at the bottom of the second sheet is a close-up view of the upper surface of a typical leaf of 'Delilah'.

DETAILED BOTANICAL DESCRIPTION

The aforementioned photographs, following observations and measurements describe plants grown in Rijpwetering, The Netherlands, in an outdoor nursery and under commercial production practices during the summer. Plants were about one year old when the photographs and description were taken. During the production of the plants, day temperatures ranged from 14 to 32° C. and night temperatures ranged from 7 to 18° C. In the following description, color references are made to The Royal Horticultural Society Colour Chart, 2001 Edition, except where general terms of ordinary dictionary significance are used.

Botanical classification: *Phlox paniculata* cultivar Delilah.

Parentage:

*Female parent.*—*Phlox paniculata* cultivar Lizzy, disclosed in U.S. Plant Pat. No. 11,574.

*Male parent.*—*Phlox paniculata* cultivar Rowie, not patented.

Propagation:

*Type.*—By terminal cuttings.

*Time to produce a rooted plant.*—About three months at 18° C.

*Root description.*—Fine; well-branched; light brown in color.

Plant description:

*Plant form/habit.*—Upright and strong plant habit; inverted triangle; moderately vigorous growth habit.

*Plant height.*—About 43 cm.

*Plant width* (*spread*).—About 40 cm.

*Lateral branches.*—Length: About 33.7 cm. Diameter: About 3 mm. Internode length: About 2.9 cm. Strength: Strong. Texture: Smooth, glabrous. Color: 144A.

*Foliage description.*—Arrangement: Opposite, simple; sessile. Length: About 8 cm. Width: About 2.9 cm. Shape: Elliptic. Apex: Acuminate. Base: Attenuate. Margin: Finely serrate. Texture, upper and lower surfaces: Smooth, glabrous. Venation pattern: Pinnate. Color: Developing leaves, upper surface: 137A; towards the margins, N186A. Developing leaves, upper and lower surfaces: 137C; towards the margins, N186A. Fully expanded leaves, upper surface: 137A. Fully expanded leaves, lower surface: 137C. Venation, upper surface: 144A to 144B. Venation, lower surface: 144B to 144C.

Flower description:

*Flower type/habit.*—Single, rounded salverform flowers arranged in terminal compound panicles; flowers face upright and outward. Freely flowering habit with about 120 flower buds and flowers per inflorescence.

*Fragrance.*—Moderate; spicy.

*Natural flowering season.*—Continuously flowering from July through September in The Netherlands. Flowers not persistent.

*Postproduction longevity.*—Flowers last about ten days on the plant or as a cut flower.

*Inflorescence height.*—About 9.3 cm.

*Inflorescence diameter.*—About 10.5 cm.

*Flower buds.*—Height: About 1.1 cm. Diameter: About 4 mm. Shape: Elliptic. Color: 157D to 150D; towards the base, 144C to 144D.

*Flowers.*—Diameter: About 3.1 cm. Depth: About 2.5 cm.

*Petals.*—Quantity per flower: Typically five in a single whorl; petals fused at the base into a narrow tube. Lobe length: About 1.7 cm. Lobe width: About 1.7 cm. Shape: Spatulate. Apex: Rounded to emarginate. Margin: Entire. Aspect: Mostly flat. Texture, upper and lower surfaces: Smooth, glabrous. Color: Developing petals, upper surface: N78A; towards the base, 71A; throat, 70A. Developing petals, lower surface: 76A to 77C; tube, 75A. Fully expanded petals, upper surface: N78A; towards the base, 71A; throat, 70A. Fully expanded petals, lower surface: 77B; tube, 77B.

*Sepals.*—Quantity per flower: Typically five in a single whorl, fused; campanulate calyx. Length: About 8 mm. Width: About 1.5 mm. Shape: Linear. Apex: Narrowly apiculate. Texture, upper and lower surfaces: Smooth, glabrous. Color, upper and lower surfaces: N186A; towards the base, 144C to 144D.

*Peduncles.*—Length: About 7.8 cm. Diameter: About 2.5 mm. Aspect: Erect to about 50° from vertical. Strength: Strong. Color: 144A occasionally tinted with reddish purple.

*Pedicels.*—Length: About 3 mm. Diameter: About 1 mm. Aspect: About 20 to 40° from vertical. Strength: Strong. Color: 144A occasionally tinted with reddish purple.

*Reproductive organs.*—Stamens: Quantity per flower: Typically five; fused with petals in tube. Filament length: About 1.5 mm. Anther shape: Oblong. Anther length: About 1.5 mm. Anther color: 4D. Pollen amount: Scarce to moderate. Pollen color: 4C to 4D. Pistils: Quantity per flower: Typically one. Pistil length: About 1.5 cm. Stigma shape: Cleft, three-parted. Stigma color: 150D. Style length: About 1.3 cm. Style color: 149B to 149C. Ovary color: 143A.

*Seed/fruit.*—Seed and fruit development have not been observed.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind, are hardy to USDA Zone 4 and tolerate temperatures as high as 35° C.

It is claimed:

1. A new and distinct cultivar of *Phlox* plant named 'Delilah', as illustrated and described.

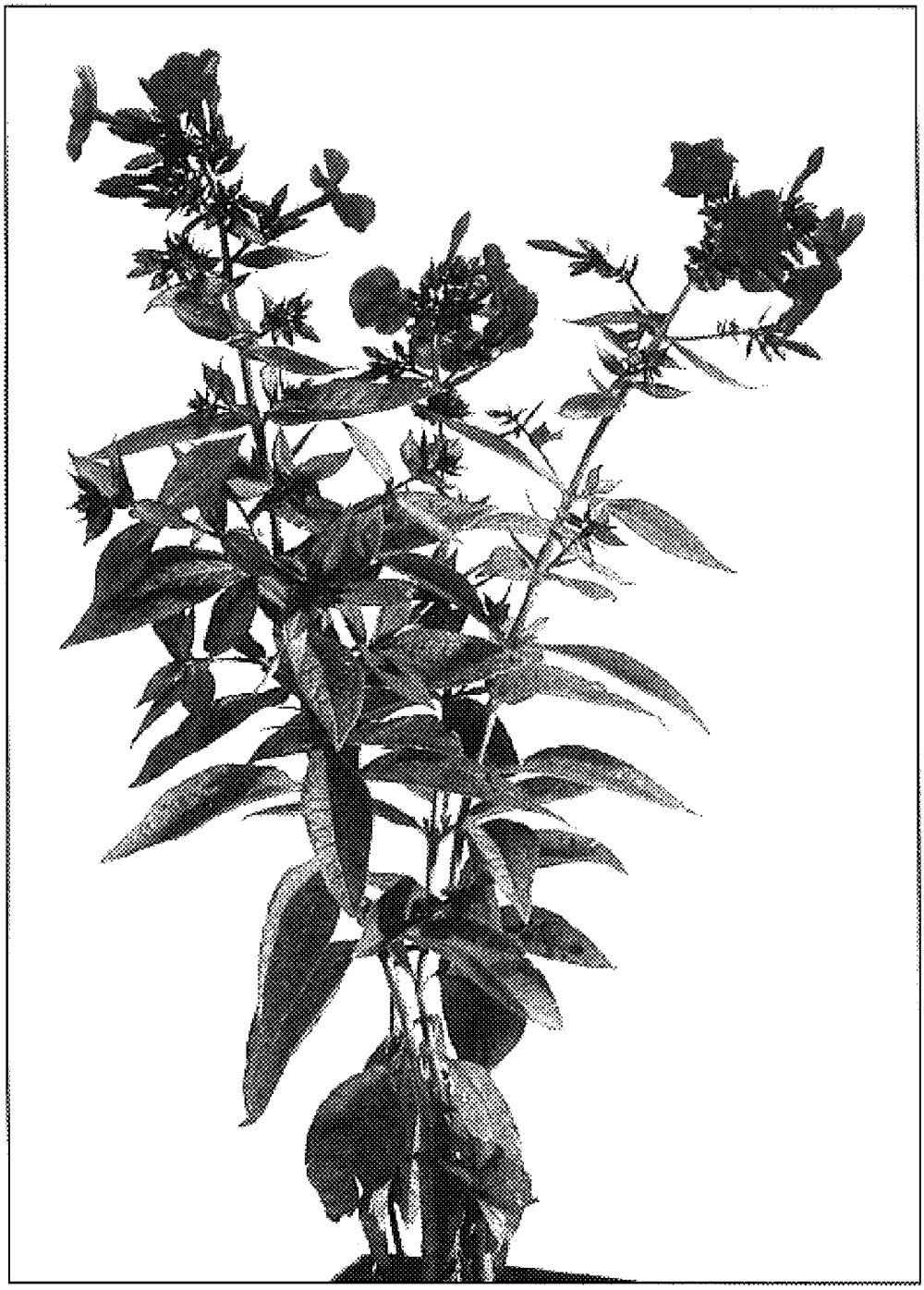

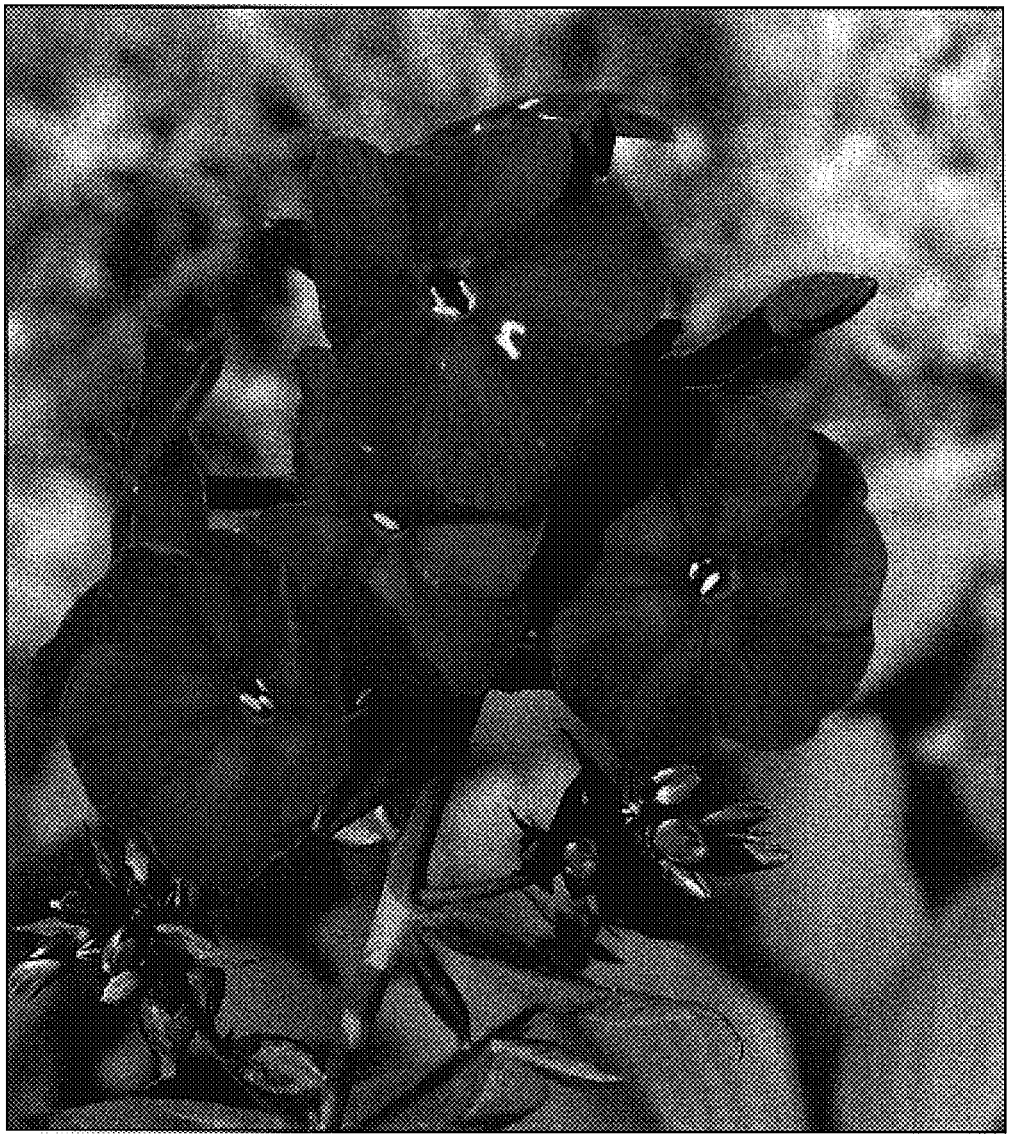
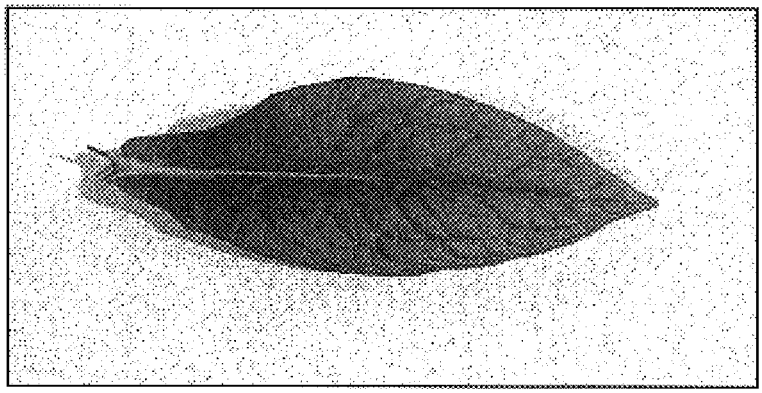

* * * * *